United States Patent
Rapp et al.

[19]

[11] Patent Number: 5,817,922
[45] Date of Patent: Oct. 6, 1998

[54] GAS SENSOR CONSISTING OF SURFACE WAVE COMPONENTS

[75] Inventors: Michael Rapp, Eppelheim; Achim Voigt, Linkenheim-Hochstetten, both of Germany

[73] Assignee: Forschungszenlram Karlsruhe GmbH, Germany

[21] Appl. No.: 751,058

[22] Filed: Nov. 15, 1996

Related U.S. Application Data

[63] Continuation-in-part of PCT/EP95/01618, Apr. 28, 1995.

[30]     Foreign Application Priority Data

May 17, 1994 [DE] Germany ............... 44 17 170.6

[51] Int. Cl.⁶ .................. G01N 29/02; G01N 29/18; G01H 13/00
[52] U.S. Cl. .................. 73/24.06; 73/23.2; 73/31.05; 310/313 R
[58] Field of Search ............... 73/23.2, 24.01, 73/24.06, 31.05, 31.06; 310/313 A, 313 R

[56]              References Cited

U.S. PATENT DOCUMENTS 4,596,697  6/1986  Ballato .................. 73/24.06 X
4,895,017  1/1990  Pyke et al. .................. 73/24.06
5,106,756  4/1992  Zaromb .................. 73/23.31 X
5,243,539  9/1993  Holt et al. .................. 73/23.2 X
5,325,704  7/1994  Mariani et al. .................. 73/24.01
5,465,608  11/1995  Lokshin et al. .................. 73/24.01

FOREIGN PATENT DOCUMENTS 8314  7/1990  WIPO .................. 73/24.06

OTHER PUBLICATIONS

Japanese Patent Abstract JP6–109710, vol. 18, No. 384, (P–1772) 19 Jul. 1994.

*Primary Examiner*—Hezron E. Williams
*Assistant Examiner*—Daniel S. Larkin
*Attorney, Agent, or Firm*—Klaus J. Bach

[57]              ABSTRACT

In a gas sensor comprising a housing and having driver and amplifier circuits the housing has a bottom part with at least four cavities arranged in radial symmetry around a central gas admission space from which gas admission passages of the same shape and size extend radially outwardly to the various cavities for supplying gas to be measured to surface wave components of which one is disposed in each of the cavities and the cavities have discharge passages extending outwardly and having all the same gas flow resistance for the discharge of the gases from the housing cavities.

4 Claims, 3 Drawing Sheets

9 X

15 Pin Sub-D Plug:
1....8 IF
9 - Mass
10 - + 10V Highly Stable
11 - Mass
12 - +12V 17nH = 7 Wdg. 0.5mm Wire, inner ⌀ = 2mm

GAS SENSOR CONSISTING OF SURFACE WAVE COMPONENTS

This is a Continuation-in-Part application of international patent application PCT/EP95/01618 of Apr. 28, 1995 claiming priority of German patent application P 44 17 170.6 of May 17, 1994.

BACKGROUND OF THE INVENTION

The invention relates to a gas sensor with surface wave components and with driver and amplifier circuits in a housing having gas admission and gas discharge means.

Modified acoustic surface wave or surface acoustic wave (SAW) components can be used for the chemical sensing of gases or fluids by providing them with a chemically reactive coating. With the ad- or absorption of an analyte the mass of the coating changes and also its elasticity parameters whereby the sound propagation speed on the surface is also changed. In order to be able to measure a change in the sound propagation speed of the surface wave as exactly and simply as possible it is common practice to include a coated SAW component as a frequency controlling element in an oscillator circuit. This is known from H. Wohltjen, R. Dessey, "SAW probe for chemical analysis", Parts 1–3; Analytical Chemistry, 51(1979), 1458–1475, and H. Wohltjen: "Mechanism of operation and Design Considerations for SAW Device Vapor Sensors"; Sensors and Actuators, 5(1984), 307–325.

With the sound speed change, an almost proportional change of the oscillation frequency is obtained which can be measured with a good resolution of typically $10^{-6}$. By a corresponding selection of sorption layers an almost unlimited amount of gaseous analytes can be examined with this technique. Of greatest interest, however, are compounds which are difficult or impossible to examine qualitatively and quantitatively with other chemical microsensors, such as organic solvents, (hexane, octane, decane, various fuels), alcohols (methanol, ethanol), halogenated hydrocarbons (CKW's, FCKW's), and aromatics (benzine, toluol).

In order to be able to analyze the compounds referred to above, substances are selected for the SAW-components which enter into a reversible sorption reaction with the respective analyte. These are mostly polymer films which can be applied to the SAW substrate by various methods such as by spin coating sol-gel-deposition or reactive deposition depending on the requirements. The sorption and dissolving behavior of the analyte in the various layers is determined by the particular ratio of their polarities, polarizing capabilities, acidity, alkalinity, and various structural parameters. However, most usable polymers suitable for coatings have too little selectivity with respect to various organic components.

EP 0 509 328 A2 discloses an arrangement of three SAW components which are however arranged in series. This leads to different flow conditions in the various sensors.

EP 0 477 684 A1 further discloses an arrangment of more than two SAW components with different coatings. A particular arrangement for the sensors is not disclosed therein.

It is the object of the invention to provide a gas sensor of the type described above by which various gas componnets can be detected at the same time.

SUMMARY OF THE INVENTION

In a gas sensor comprising a housing and having driver and amplifier circuits the housing has a bottom part with at least four cavities arranged in radial symmetry around a central gas admission space from which gas admission passages of the same shape and size extend radially outwardly to the various cavities for supplying gas to be measured to surface wave components of which one is disposed in each of the cavities and the cavities have discharge passages extending outwardly and having all the same gas flow resistance for the discharge of the gases from the housing cavities.

By a combination of several sensors with coatings of different properties, sensitivity samples can be obtained which, following a chemometrical evaluation (PLS algorithm), permit the desired qualitative and quantitative determination also of a mixture of analytes. By utilizing the Linear Solvation Energy Relationship (LSER) models, it is further possible to make a theoretical prediction of the sorption properties of various coating materials. This permits a calculated optimization by a selection of the coating substances or, respectively, their combination. With a coating system so provided, selective determinations of a variety of gaseous organic analytes is achievable.

Minimal conductor lengths by radial connections extending from a common nodal point result in low signal losses by attenuation and small chances for inductive disturbances in the various channels.

A radial arrangement of the gas admission lines also provides, in a most simple manner, for an equivalent, parallel and synchronous admission of the test gases. This is a decisive advantage for the signal evaluation with the chemometrical evaluation processes and with evaluation processes using automatic reaction sample recognition by neural networks.

Below, the invention will be described in greater detail on the basis of the enclosed figures.

DESCRIPTION OF PREFERRED EMBODIMENTS

Figure 1A:
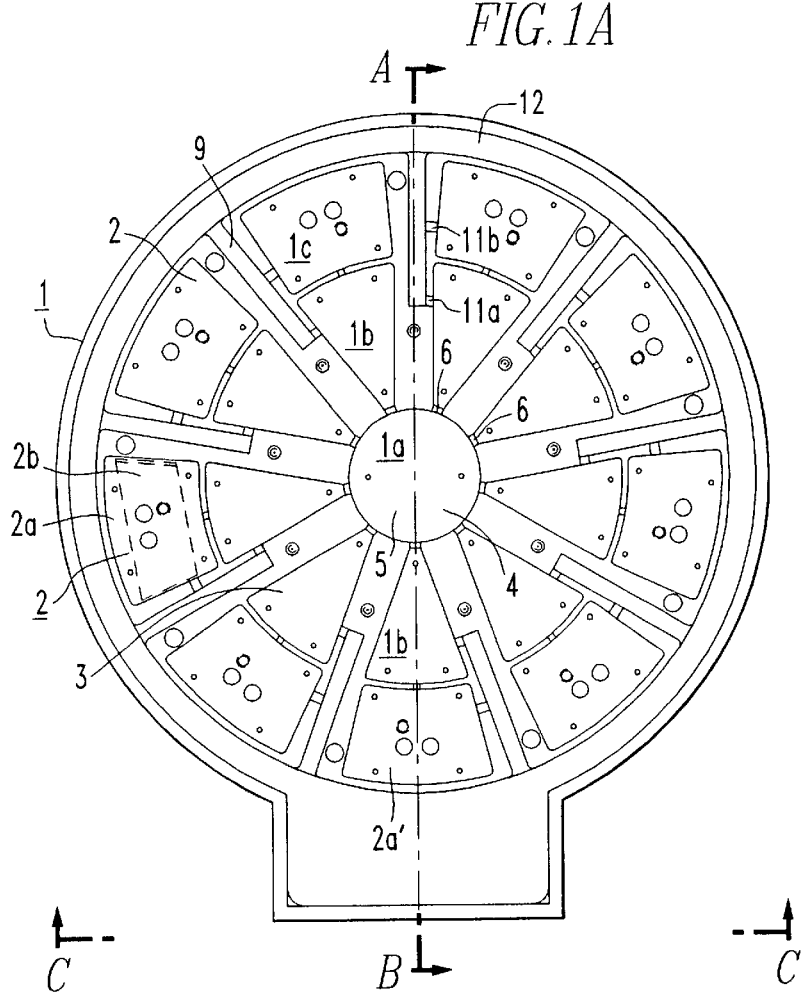
FIGS. 1A, 1B, and 1C show the bottom part of a housing receiving the SAW components and an electronic module and, FIGS. 2, 3, and 4 show the circuitry used in the module.
Figure 1B:
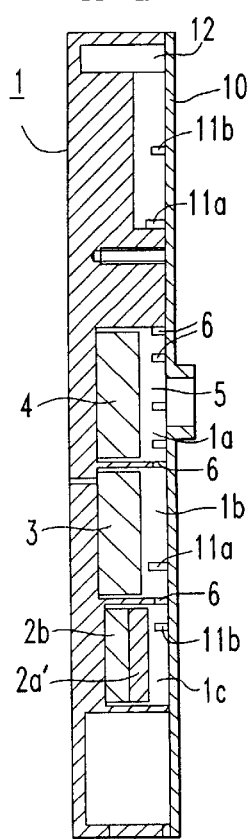

FIG. 1A is a plane view of the bottom part 1 of the housing on which the electronic modules 2, 3, and 4 are disposed in cavities 1a, 1b, and 1c formed therein. FIG. 1B is a cross-sectional view taken along line A–B of FIG. 1. The SAW components 2b are disposed on the back side of the modules 2 behind the oscillations 2a. They are indicted in FIG. 1A by dashed lines. This SAW sensor arrangement for the analytical determination of gases and gas mixtures comprises 9 SAW oscillator, modules 2 wherein one of the oscillator 2a serves as common reference for 8 sensor oscillators. However, the arrangement can be expanded to n oscillators with a common reference oscillator 2a' and n–1 sensor oscillators wherein n should be greater than 3.

The signal of the reference oscillator is distributed to the various (n–1) mixing stages 3 by way of a common impedence-adapted jointure (power splitter circuit 4). The arrangement with a common nodal point facilitates the control of the various mixer imputs with the same HF level.

Figure 1C:
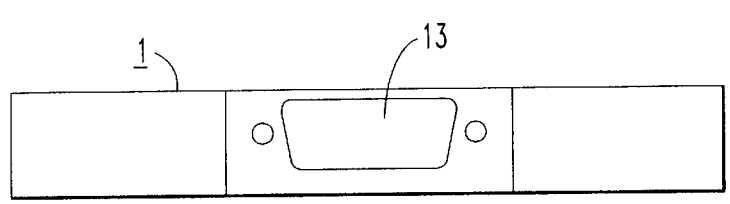

The housing bottom part 1 and the housing top part 10 which is shown only in FIG. 1B, both consist of metal. The housing top part 10 defines a central rotation-symmetrical gas admission chamber 5 from which identical radial gas admission lines 6 lead to cavities 1b and 1c in which the SAW sensors oscillator and sensor modules 2 are disposed. From those cavities 1b, 1c, gas discharge passages 11a, 11b, all with the same flow resistance, lead to the outside via radial passages 9 and a collection channel 12. FIG. 1C is a view of the housing part 1 in the direction of the arrows C showing the discharge opening 13 through which gases collected in the collection channel 12 are discharged from the housing 1.

The high heat conductivity of the metal housing facilitates a uniform temperature distribution throughout the whole housing while the manufacturing costs are relatively low and the arrangement is compact and allows for good mobility.

With parallel gas admission and small sample volumina, short reaction times are achieved.

The setup of the SAW oscillators in a common compact monolithic housing including various chambers which contain the various oscillator circuits and, separately therefrom in different chambers the mixing stages, an even better temperature distribution (high heat conductivity of the housing) and a lower inductive disturbances are achieved so that there is no great chance that adjacent oscillation frequencies are transferred since there is an optimal shielding of the housing which is on mass potential.

Generally, the commercially manufactured transducers consist of aluminum (best acoustic-electrical properties) which is chemically not sufficiently resistent to provide for an extended stable operation of a SAW-chemo sensor. For this reason gold is for example better suited as transducer material in the SAW gas sensor technology. Another possibility is the subsequent chemical passivation of the aluminum transducer by controlled oxidation of the aluminum or by an inert material coating (for example, polyimide) of the transducer.

As a substrate for SAW building component, quartz has, depending on the selection of the crystal cut, a certain temperature with smallest temperature variation for the surface wave sound speed, that is, the so-called compensation temperature. If this temperature is selected as the operating temperature for the arrangement, a low disturbance sensitivity with respect to small temperature changes is achieved.

In accordance with the Linear Solvation Energy Relationship (LSER)-model, there are five energetically different components which determine the dissolution behavior of an organic solvent into a solid phase. For the bonding enthalpies, an analytical relationship can be formulated (formula 9, p. 95 of J. W. Grate, M. H. Abraham: "SOLUBILITY INTERACTIONS AND THE DESIGN OF CHEMICALLY SELECTIVE SORBENT COATINGS FOR CHEMICAL SENSORS AND ARRAYS", Sensors and Actuators B, 3(1991), 85–111).

The various energy terms can be characterized by solubility parameters wherefrom five parameters can be established for the gaseous phase and five additional corresponding parameters for the solid phase. These parameters in a way represent a weighting of the energy terms responsible for the dissolution process. They are different for the various compounds.

An optimal layer system includes layer substances in the various layers with an as different parameter combination as possible. For a sensor array with such a layering system, very good differentiation capabilities can be expected.

If substances can be found which have parameters at the extremes that is, ideally, wherein one parameter is at maximum and another is at minimum value, the number of layers required for a differentiation parameter can be reduced to the number of responsible parameters, that is to five.

The table shows, as examples, substances for which this condition applies and, consequently, represents a selection of substances. The actual values are shown in the center. The value comparison on the right hand side shows that some values in each case are maximal whereas the corresponding sizes are minimal. Inspite of the low number of sensors with such a SAW sensor array in principle, the best possible analyses by chemometrical sample recognition can be achieved.

With the most favorable number of eight sensor oscillators and one common reference oscillator in the array, three additional sensors are provided to analyze typical disturbances. As a result, for compounds with interfering components, a greater redundancy is achieved whereby mixtures which include interfering components such as water, nitrogen oxides, and ammonia, can be determined more significantly.

The array and its evaluation is optimal for eight signal values since digital electronic evaluation circuits on commercially available microchips generally have 8 bit-multiple rasters.

Because of the large influence temperature has on the oscillator frequencies, the temperature of the sensor head must be maintained highly constant. With the compact sensor head design, it is possible to control, by way of Peltier-elements, the temperature of the gases to be measured and that of the sensors as well as the electronic controls precisely over a large range.

The equilibrium distribution between analyte in the gas phase and analyte in the solid phase (absorbed) depends on the temperature. At low temperature, the equilibrium adjustment is closer to the absorbed phase whereby a higher sensor sensitivity is provided. At higher temperatures, the relationship is inversed. The equilibrium distribution is closer to the gas phase and the sensor becomes less sensitive. For On the other hand, the equilibrium conditions are obtained more rapidly.

Accordingly, by the selection of the operating temperature of the sensor head, the sensitivity and the response behavior can be adapted to the required specifications.

It is advantageous to provide for a temperature control by providing Peltier-elements directly on the housing cover. The waste heat can then be transferred directly to the environment by means of convective heat transfer structures provided on the element or indirectly, in a more effective way, by a pumped liquid coolant circuit.

If the temperature is controlled by means of a liquid heat transfer medium (for example water), then the temperature of the liquid is controlled by an external temperature control unit before it is circulated through the liquid coolant circuit.

The various particular SAW sensors in the array are disposed on the respective oscillator electronic devices in a plug-in fashion. As basis herefor the commercially available TO sockets (for example, TO-39) may be used into which the SAW components can be inserted. The array is then simple, easy to assemble, and relatively inexpensive and can be easily adapted for various applications (various analyte compositions). The individual sensors are also easy to test during servicing or control procedures.

For applying different coatings to the sensors, the spin coating process is suitable since the SAW components which are already mounted on sockets and connected to contact pins can be inserted centrally onto the axis of a spin coating apparatus.

The coating however can also be applied by spraying.

Figure 2:
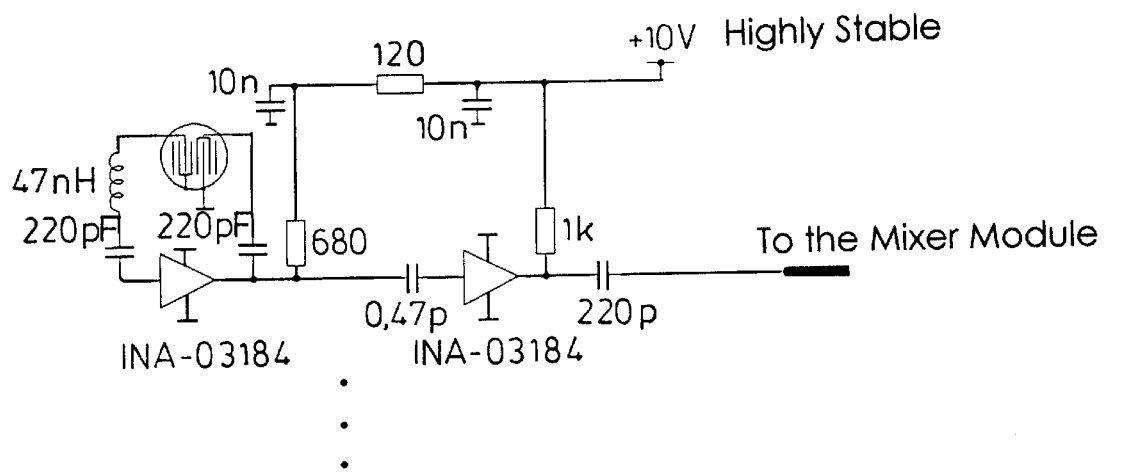

FIG. 2 shows a circuit arrangement for an optimal SAW oscillator circuit 2 which has an improved signal to noise ratio (higher sensitivity), a lower detection limit and a better long-time stability of the SAW sensors as compard with the oscillator circuit referred to below.

A. Venema et al., "DESIGN ASPECTS OF SAW GAS SENSORS", Sensors and Actuators, 10 (1986, p. 47–64) already describes an optimized oscillator circuit for SAW-gas sensor techniques which utilizes a so-called AGC (automatic gain control). It is believed, however, that this circuit has no essential advantages since, with the automatic adaption of the amplification factor, phase drifts develop which result in an undesirable frequency drift in the oscillator circuit. The adaptation of the amplification factor said to be necessary in this publication can be realized practically only at frequencies below 200 Mhz and at great expenditures. It is however, not needed with the use of SAW components with suitable transmission characteristics.

For the development of a SAW oscillator, the special behavior of coated and uncoated SAW resonators on quartz basis has to be taken into consideration. Coated SAW oscillators have a high attenuation and a small phase change at the resonance point. The active oscillator electronic circuit has to be designed in such a way that, on one hand, it provides for a sufficiently high amplification to compensate for the attenuation and, on the other hand, it can follow, in its frequency-phase behavior, the change of the frequency phase behavior of the coated SAW oscillator so as to maintain the electric oscillation conditions.

This condition is fulfilled by the MMIC amplifier INA-03148. Its S parameters at 433 Mhz provide, in a combination with a 47 nH coil, for an optimal transmission characteristic of the active oscillator element with a current consumption of only 7 mA. By way of the 220 pF condensers, the high frequency is coupled into, or out of, the SAW component.

The oscillator frequency is uncoupled at the exit of the oscillator amplifier by way of a 0.47 pF condensor with high impedance and is supplied to a subsequently arranged buffer amplifier. In this way, the sensitive oscillator cirucuit is separated electrically from the rest of the circuit by its high reverse isolation (S12) so that the influence of spurious signals or impedance changes on the oscillation frequency remain at a minimum.

The oscillator electronic circuitry is arranged in immediate proximity with the SAW sensors. The SAW components are plugged directly onto the oscillator electronic circuits.

An oscillator circuit is extremely sensitive to variations of the phase relationships which can occur in the resonance circuit by even small impedance changes. In practice, the cause for such changes are mainly movable conduits. For this reason, no such conduits are employed.

The electro-acoustic parameters and consequently, the phase relationship and the attenuation of the SAW sensors change depending on the coating parameters. The oscillator electronic circuit can tolerate such parameter changes and may have a sufficient frequency stability (±2½ at 433.92 Mhz oscillation frequency) without new calibration.

By a good selection of amplifiers with minimal phase relationship on S parameters which are attuned to the SAW sensors, the desired characteristics could be achieved. These conditions are also fulfilled by wide band amplifiers such as various video amplifiers.

Figure 3:
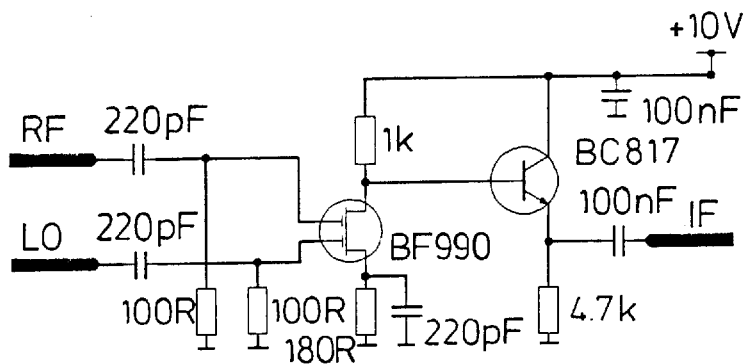

FIG. 3 shows a circuit for a dual gate mixer 3. The frequencies of measurement oscillators and reference oscillators are mixed in mixers down to a lower-value intermediate frequency and are subsequently counted by a electronic counter.

As mixing circuit, a dual gate EET was selected with subsequent collector circuit as impedance converter.

This has the following advantages:
a) also small input signals are mixed linearly;
b) the impedance of the mixer inputs can be freely selected, in limits, by way of the gate resistances,
c) there is a low current consumption (about 5 mA);
d) there is a low output resistance (about 100Ω);
e) the steep slopes of the mixer imputs provide at the same time for an amplification of the mixer product;
f) SMD or hybrid techniques can be utilized.

Figure 4:
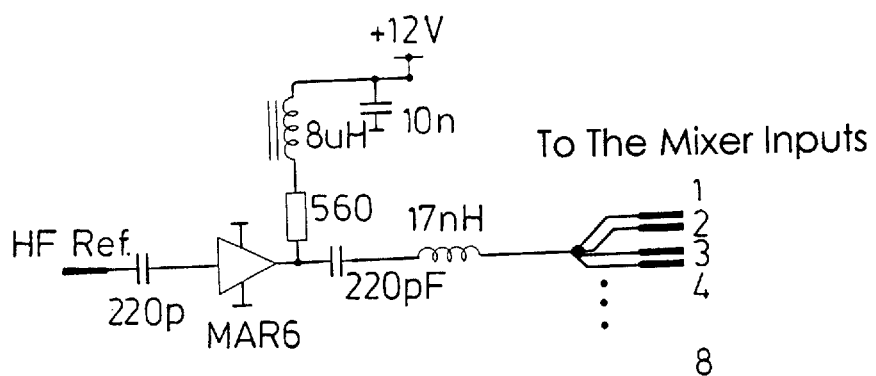

FIG. 4 shows a circuit for a power splitter 4.

The signal of the reference oscillator is amplified and is supplied to a central connecting point with the impedance 12.5Ω. The coil which is arranged in the line to the amplifier exit adapts the impedance of the 50Ω amplifier output to the central connecting point. From the central connecting point the reference signal is distributed to eight mixer inputs with an input impedance of 100Ω each.

With the use of suitable SAW components, the following advantages are achieved:
a) there is a steep phase slope at the resource point,
b) there is a small increase in the input attenuation if a coating is present. This is achieved mainly by special SAW delay conduits which have a great transducer length. The frequency remains unchanged in this case by the active transducer structure and is less negatively influenced by a coating as this is the case with the SAW resonators.
c) there is generally little blend-in attenuation independently of the coating. This provides for a correspondingly small amplification in the oscillation circuit and provides for a better signal-noise ratio of the whole oscillator;
d) components with transmission frequencies of 250–500 Mhz are used. In this measuring range an optimum of sensitivity ($\approx f^2$), signal to noise ratio ($\approx f$) and operability ($\approx 1/f$) is obtained.

By the use of electronic components with extremely low power consumption, the undesirable heating of the SAW sensors is limited. The amplifier type mentioned earlier, most other alternatives and the usually employed components for the mixing stage which include the so-called "double balanced mixers" have a relatively high power consumption. This results in a greater thermal load for the SAW sensors. The thermal load becomes increasingly problematic particularly with respect to a miniaturization of the whole array since the necessary thermal pre-conditioning of the sample gas where being supplied to the sensors would becomee too complicated or impossible.

So-called MMIC (microwave monolithic integrated circuit) amplifiers have a substantially lower power consumption. The type INA03184 circuit by Advantac USA was found to be particularly advantageous. Its use results in a power consumption per oscillator module of only 120 mW.

With an active dual gate FET mixer circuit instead of the usual circuit with "double balanced mixers", the normally required electronic control circuitry can be omitted whereby the power consumption per mixer module can be reduced to 50 mW.

The compact design with a surface area of about 1 cm² is obtained by a full utilization of SMD components and by an optimal circuit layout. With this measure, the circuits are well suited for the combination of several SAW sensors to form the gas sensor according to the invention.

What is claimed is:

1. A gas sensor comprising: a housing and having driver and amplifier circuits, said housing having formed in a bottom part thereof at least four cavities arranged in a circle around a center area of said housing in radial symmetry, a surface wave acoustic component disposed in each of said at least four cavities, a central gas admission space formed in the center area of said housing, gas admission passages extending radially outwardly from said central gas admission space to said cavities, said gas admission passages being arranged in radial symmetry and having all the same shape and the same length and gas discharge passages extending outwardly from said cavities and having all the same gas flow resistance.

2. A gas sensor according to claim 1, wherein immediately adjacent each surface wave acoustic component and on top of said surface wave acoustic component, there is arranged an oscillator circuit connected to the respective adjacent surface wave acoustic component.

3. A gas sensor according to claim 1, wherein one of said surface wave acoustic components serves as a common reference for the other surface wave acoustic components.

4. A gas sensor according to claim 1, wherein said housing includes nine cavities arranged in radial symmetry each receiving one surface wave acoustic component.

* * * * *